United States Patent
Toreki et al.

(10) Patent No.: US 7,473,474 B2
(45) Date of Patent: Jan. 6, 2009

(54) ANTIFUNGAL GYPSUM BOARD

(75) Inventors: William Toreki, Gainesville, FL (US); Gerald Olderman, Bedford, MA (US); Gregory Staab, Ventura, CA (US)

(73) Assignee: Quick-Med Technologies, Inc., Gainesville, FL (US)

( * ) Notice: Subject to any disclaimer, the term of this patent is extended or adjusted under 35 U.S.C. 154(b) by 0 days.

(21) Appl. No.: 10/546,850

(22) PCT Filed: Feb. 25, 2004

(86) PCT No.: PCT/US2004/005616

§ 371 (c)(1),
(2), (4) Date: Aug. 24, 2005

(87) PCT Pub. No.: WO2004/076770

PCT Pub. Date: Sep. 10, 2004

(65) Prior Publication Data

US 2006/0194072 A1    Aug. 31, 2006

Related U.S. Application Data

(60) Provisional application No. 60/449,915, filed on Feb. 25, 2003.

(51) Int. Cl.
B32B 23/04 (2006.01)

(52) U.S. Cl. ................. 428/536; 428/537.7; 514/255; 427/326

(58) Field of Classification Search ............... 428/536, 428/537.7; 514/255; 427/326
See application file for complete search history.

(56) References Cited

U.S. PATENT DOCUMENTS

| | | | |
|---|---|---|---|
| 3,778,476 A | 12/1973 | Rembaum et al. | |
| 3,898,336 A | 8/1975 | Rembaum et al. | |
| 3,945,842 A | 3/1976 | Green | |
| 4,027,020 A | 5/1977 | Green et al. | |
| 4,076,663 A * | 2/1978 | Masuda et al. | 525/54.31 |
| 4,379,890 A | 4/1983 | Konietzny et al. | |
| 4,970,211 A | 11/1990 | Fenyes et al. | |
| 5,049,383 A | 9/1991 | Huth et al. | |
| 5,051,124 A | 9/1991 | Pera | |
| 5,091,102 A | 2/1992 | Sheridan | |
| 5,432,000 A | 7/1995 | Young, Sr. et al. | |
| 5,658,915 A * | 8/1997 | Abe et al. | 514/252.11 |
| 5,700,742 A | 12/1997 | Payne | |
| 5,856,248 A | 1/1999 | Weinberg | |
| 6,126,931 A | 10/2000 | Sawan et al. | |
| 6,146,688 A | 11/2000 | Morgan et al. | |
| 6,803,420 B2 | 10/2004 | Cleary et al. | |
| 7,045,673 B1 | 5/2006 | Batich et al. | |
| 7,056,460 B2 * | 6/2006 | Englert | 264/86 |
| 2002/0177828 A1 | 11/2002 | Batich et al. | |
| 2003/0035981 A1 * | 2/2003 | Capps | 514/252.11 |
| 2005/0003163 A1 * | 1/2005 | Krishnan | 428/190 |
| 2005/0033251 A1 | 2/2005 | Toreki et al. | |

FOREIGN PATENT DOCUMENTS

| | | |
|---|---|---|
| DE | 147949 | 12/1979 |
| EP | 0493970 | 7/1992 |
| GB | 497958 A | 12/1938 |
| GB | 818412 | 8/1959 |
| GB | 1461909 | 1/1977 |
| GB | 2300200 | 10/1996 |
| GB | 2408516 | 6/2005 |
| JP | 10-237763 | 9/1998 |
| WO | 98/21253 | 5/1998 |
| WO | 99/32157 | 7/1999 |

OTHER PUBLICATIONS

Lee, Sang Beom; Koepsel, Richard R.; Morley, Scott W.; Matyjasezewski, Krzysztof; Sun, Yujie; Russell, Alan J.; "Permanent, Nonleaching Antibacterial Surfaces" 1. Synthesis by Atom Transfer Radial Polymerization, Biomacromolecules 2004, 5 pp. 877-882, 2004 American Chemical Society.

(Continued)

*Primary Examiner*—Leszek Kiliman
(74) *Attorney, Agent, or Firm*—Gerry J. Elman; Elman Technology Law, P.C.

(57) ABSTRACT

A novel improved gypsum board having improved antifungal properties is disclosed. The board comprises a gypsum core, front and back paper facings and a polymeric antifungal agent effective at inhibiting fungal growth. A preferred polymeric antifungal agent is polyDADMAC or polyTMMC. In addition to the polymeric antifungal agent, a non-polymeric antifungal agent, such as cetyl pyridinium chloride, sodium or zinc pyrithione, or both, may be included. The polymeric antifungal agent can be present in the gypsum core and/or on one or both of the paper facings. In addition, the antifungal agent may be encapsulated in a material or ionically associated with the polymeric antifungal agent, that releases the antifungal agent over time and/or upon exposure to moisture. Also disclosed are methods for preparing the aforementioned improved antifungal gypsum board.

15 Claims, No Drawings

OTHER PUBLICATIONS

Abel, Tanya; Cohen, Jaimelee Iolani; Engel, Robert; Filshtinskaya, Maya; Melkonian, Alice; Melkonian, Karen; Preparation and investigation of antibacterial carbohydrate-based surfaces, Carbohydrate Research 337 (2002) pp. 2495-2499.

Onabe, Fumihiko; "Studies on Interfacial Properties of Polyelectrolyte-Cellulose Systems, I. Formation and Structure of Adsorbed Layers of Cationic Polyelectrolyte-(Poly-DMDAAC) on Cellulose Fibers", Journal of Applied Polymer Science, vol. 22, 3495-3510 (1978) John Wiley & Sons, Inc.

Wallace, Michele L., "Testing the Efficacy of Polyhexamethylene Biguanide as an Antimicrobial Treatment for Cotton Fabric" AATCC Review, Nov. 2001, pp. 18-20.

* cited by examiner

ANTIFUNGAL GYPSUM BOARD

BACKGROUND OF THE INVENTION

1. Technical Field of the Invention

The present invention relates generally to gypsum board and methods for making gypsum board. More specifically, the present invention relates to improved gypsum board possessing antifungal properties and improved methods of making the same.

2. Description of Related Art

Gypsum board, which is sold as wallboard and drywall, is a common building material used in various applications including interior walls, partitions and ceiling construction. Commercial gypsum board products are popular for a variety of reasons. They are durable, economical and fire-retardant. In addition, these boards provide excellent compressive-strength properties and a relatively low density. Finally, they are easily decorated and are therefore attractive as surfacing materials, especially for interior construction.

One fundamental limitation of traditional gypsum board products is their susceptibility to moisture absorption in damp environments. To minimize this problem, gypsum board is normally used in interior construction where exposure to moisture is limited. Unfortunately, products used in interior construction sometimes encounter water due to seepage, leaky roofs or pipes, flooding, condensation, and the like, arising out of construction defects or other events unrelated to the manufacture of the gypsum board. Thus, a number of mechanisms result in the exposure of gypsum board products to moisture. Once exposed to moisture, traditional gypsum board products are susceptible to fungal growth.

In patent publication number US2003/0035981 and US2003/0031898, there are disclosed antifungal gypsum boards in which monomeric antifungal agents are included in components of wallboard materials. Due to the monomeric nature of the antifungal agents, such as the preferred antifungal agents of those disclosures, cetyl pyridinium chloride, those patent publications discuss the inclusion of binders, retention aids, encapsulants and the like, for retaining the monomeric antifungal agents in association with the gypsum board components. The present invention provides an improved antifungal gypsum board by disclosing polymeric compounds which are antifungal and which therefore have enhanced antifungal efficacy and retention in the gypsum board components. We have also found that polymeric quaternary amines are significantly more antimicrobial than are monomeric quaternary amines.

There is an ongoing need for gypsum board products that offer reduced susceptibility to fungal growth without compromising their beneficial properties. In addition, there is an ongoing need for commercially viable manufacturing methods for such products. The present invention solves these problems by using an improved antifungal agent that effectively inhibits fungal growth, is compatible with gypsum board materials, and can be incorporated into a cost-effective and commercially-viable manufacturing process.

BRIEF SUMMARY OF PREFERRED EMBODIMENTS

The preferred embodiments of the present invention include a novel gypsum board comprising an effective amount of an antifungal agent such that fungal growth on or in the board is inhibited. According to a preferred embodiment of the present invention, the antifungal agent is a polymeric antifungal agent (PAA), alone or in combination with a monomeric antifungal agent, such as cetyl pyridinium chloride (CPC), a quaternary ammonium compound, or a pyrithione, such as sodium pyrithione, (SP), or another anionic antifungal compound which binds ionically to a cationic PAA, and be thereby more effectively retained than if the pyrithione were simply mixed with or adsorbed to wallboard components. Preferably, the gypsum board comprises from about 0.01 to about 5 weight percent PAA and CPC or SP based on the dry weight of the gypsum in the board. More preferably, the gypsum board comprises between about 0.5 and about 1.0 weight percent PAA and CPC or SP based on the dry weight of the gypsum in the board. According to some preferred embodiments, the PAA and CPC or SP are encapsulated in an encapsulator so that it is released over time and/or upon exposure to moisture.

The preferred embodiments of the present invention also include methods of preparing the novel gypsum board described above. According to some preferred embodiments, PAA alone or PAA and CPC or SP are incorporated onto or into the gypsum core by premixing PAA with or without CPC or SP with the water, premixing the PAA with or without CPC or SP with the gypsum powder, admixing the PAA with or without CPC or SP with both the water and gypsum powder prior to or in the slurry mixer, and/or adding PAA with or without CPC or SP to a mixed gypsum slurry via a secondary or in-line mixer. According to other preferred embodiments, a PAA with or without CPC or SP solution is sprayed onto the front and/or back paper facings.

According to other preferred embodiments, PAA with or without CPC or SP is incorporated into the front and/or back paper facings as they are manufactured.

In another preferred embodiment the PAA is a polymeric quaternary amine.

In another preferred embodiment, the PAA is covalently bonded to components of the gypsum, the front paper facing, the back paper facing or both.

In another preferred embodiment, the PAA is a polymeric quaternary amine which binds an anionic antimicrobial agent, such as SP, thereby improving the retention of the SP in association with the wallboard.

DETAILED DESCRIPTION OF PREFERRED EMBODIMENTS

The present invention derives from the discovery that an improved effective antifungal agent exhibits compatibility with gypsum board without diminishing the qualities of the gypsum board. Preferably, the mechanical properties of the gypsum board such as density, break strengths, bond strength, core end and edge hardness, modulus of flexibility and the like are substantially unchanged by the addition of the antifungal agent. By substantially unchanged, a given mechanical property preferably remains within the parameters of governing standards—e.g., ASTM standards. Consequently, the improved novel gypsum board product achieves the structural, economic and other benefits of gypsum board while also offering significant resistance to fungal growth. The novel gypsum board product can be prepared according to methods that are cost-effective and commercially viable.

The preferred embodiments of the present invention include a novel gypsum board comprised of a gypsum core, paper surfacing bonded to both sides of the core, and an antifungal agent. Any material suitable as a gypsum core is within the scope of the present invention. Therefore, without limiting the scope of the invention, the preferred embodiments comprise a gypsum core comprised of gypsum powder, water and optionally foam, pulp, starch and/or set controlling agents. Typically, the gypsum core is sandwiched between two sheets that are commonly referred to as the front and back paper facings. The front paper facing is generally a light-colored, smoothly textured paper designed to face into the interior of the building. The back paper facing, in contrast, is typically a darker, less smoothly-textured paper designed not to be seen. Any material suitable as a front and/or back paper facing is within the scope of the present invention. Therefore, without limiting the scope of the invention, the preferred embodiments comprise front and back paper facings comprised of a cellulosic material.

The preferred embodiments of the present invention also employ an improved antifungal agent, as used herein meaning and including all agents, materials, and combinations thereof providing antimicrobial activity. Preferred antimicrobial agents are those of the type and in an amount effective for inhibiting the growth and/or formation of microbes such as bacteria and/or fungi. Any known antifungal agent compatible with gypsum board composition and manufacturing processes and providing the desired biocidal, antifungal, antimycogen, antibacterial, and/or like activity in the gypsum board may be employed with the present invention. As will be readily apparent to one of skill in the art, a variety of antifungal agents are known including, for example, chlorhexidine, alexidine, cetyl pyridinium chloride, benzalkonium chloride, benzethonium chloride, cetalkonium chloride, cetrimide, cetrimonium bromide, glycidyl trimethylammonium chloride, stearalkonium chloride, hexetidine, triclosan and triclocarban. The improved antifungal agent of this invention, however, is a polymeric antifungal agent, comprising at least two monomeric units, and up to a thousand monomeric units, covalently linked to each other. The polymeric antifungal agent may be used alone or in combination with monomeric antifungal agents known in the art, such as quaternary ammonium compounds, including but not limited to the following compounds:

Fluoride:
Tetra-n-butylammonium Fluoride
Tetraethylammonium Fluoride

Chloride:
Acetylcholine Chloride
(3-Acrylamidopropyl)trimethylammonium Chloride
Benzalkonium Chloride
Benzethonium Chloride
Benzoylcholine Chloride
Benzylcetyldimethylammonium Chloride
N-Benzylcinchonidinium Chloride
N-Benzylcinchoninium Chloride
Benzyldimethylphenylammonium Chloride
Benzyldimethylstearylammonium Chloride
N-Benzylquinidinium Chloride
N-Benzylquininium Chloride
Benzyltri-n-butylammonium Chloride
Benzyltriethylammonium Chloride
Benzyltrimethylammonium Chloride
Carbamylcholine Chloride
DL-Carnitine Hydrochloride
Chlorocholine Chloride
(3-Chloro-2-hydroxy-n-propyl)trimethylammonium Chloride
Choline Chloride
n-Decyltrimethylammonium Chloride
Diallyldimethylammonium Chloride
Dichloromethylenedimethyliminium Chloride
Dimethyldistearylammonium Chloride
n-Dodecyltrimethylammonium Chloride
Girard's Reagent T
n-Hexadecyltrimethylammonium Chloride
Hexamethonium Chloride
Lauroylcholine Chloride
Methacholine Chloride
Methacroylcholine Chloride
(2-Methoxyethoxymethyl)triethylammonium Chloride
beta-Methylcholine Chloride
Methyltriethylammonium Chloride
Myristoylcholine Chloride
n-Octyltrimethylammonium Chloride
Phenyltriethylammonium Chloride
Phenyltrimethylammonium Chloride
Phosphocholine Chloride Calcium Salt
Phosphocholine Chloride Sodium Salt
Succinylcholine Chloride
Tetra-n-amylammonium Chloride
Tetra-n-butylammonium Chloride
Tetradecyldimethylbenzylammonium Chloride
n-Tetradecyltrimethylammonium Chloride
Tetraethylammonium Chloride
Tetramethylammonium Chloride
Trimethyl[2,3-(dioleyloxy)propyl]ammonium Chloride
Trimethylstearylammonium Chloride
Trioctylmethylammonium Chloride
Tri-n-octylmethylammonium Chloride Bromide:
Acetylcholine Bromide
Benzoylcholine Bromide
Benzyltri-n-butylammonium Bromide
Benzyltriethylammonium Bromide
Bromocholine Bromide
Cetyldimethylethylammonium Bromide
Choline Bromide
Decamethonium Bromide
n-Decyltrimethylammonium Bromide
Didecyldimethylammonium Bromide
Dilauryldimethylammonium Bromide
Dimethyldimyristylammonium Bromide
Dimethyldioctylammonium Bromide
Dimethyldipalmitylammonium Bromide
Dimethyldistearylammonium Bromide
n-Dodecyltrimethylammonium Bromide
(Ferrocenylmethyl)dodecyldimethylammonium Bromide
(Ferrocenylmethyl)trimethylammonium Bromide
n-Hexadecyltrimethylammonium Bromide
Hexamethonium Bromide
Hexyldimethyloctylammonium Bromide
n-Hexyltrimethylammonium Bromide
Methacholine Bromide
Neostigmine Bromide
n-Octyltrimethylammonium Bromide
Phenyltrimethylammonium Bromide
Stearyltrimethylammonium Bromide
Tetra-n-amylammonium Bromide
Tetra-n-butylammonium Bromide
Tetra-n-decylammonium Bromide
n-Tetradecyltrimethylammonium Bromide
Tetraethylammonium Bromide
Tetra-n-heptylammonium Bromide
Tetra-n-hexylammonium Bromide
Tetramethylammonium Bromide
Tetra-n-octylammonium Bromide
Tetra-n-propylammonium Bromide
3-(Trifluoromethyl)phenyltrimethylammonium Bromide
Trimethylvinylammonium Bromide Valetharnate Bromide Iodide:
Acetylcholine Iodide
Acetylthiocholine Iodide
Benzoylcholine Iodide
Benzoylthiocholine Iodide
Benzyltriethylammonium Iodide
n-Butylylcholine Iodide
n-Butyrylthiocholine Iodide
Decamethonium Iodide
N,N-Dimethylmethyleneammonium Iodide
Ethyltrimethylammonium Iodide
Ethyltri-n-propylammonium Iodide
(Ferrocenylmethyl)trimethylammonium Iodide
(2-Hydroxyethyl)triethylammonium Iodide
beta-Methylcholine Iodide
O-.beta.-Naphthyloxycarbonylcholine Iodide
Phenyltriethylammonium Iodide
Phenyltrimethylammonium Iodide
Tetra-n-amylammonium Iodide
Tetra-n-butylammonium Iodide
Tetraethylammonium Iodide
Tetra-n-heptylammonium Iodide
Tetra-n-hexylammonium Iodide
Tetramethylammonium Iodide
Tetra-n-octylammonium Iodide
Tetra-n-propylammonium Iodide
3-(Trifluoromethyl)phenyltrimethylammonium Iodide Hydroxide:
Benzyltriethylammonium Hydroxide
Benzyltrimethylammonium Hydroxide
Choline
n-Hexadecyltrimethylammonium Hydroxide
Phenyltrimethylammonium Hydroxide
Sphingomyelin
Tetra-n-butylammonium Hydroxide
Tetra-n-decylammonium Hydroxide
Tetraethylammonium Hydroxide
Tetra-n-hexylammonium Hydroxide
Tetramethylammonium Hydroxide
Tetra-n-octylammonium Hydroxide
Tetra-n-propylammonium Hydroxide
3-(Trifluoromethyl)phenyltrimethylammonium Hydroxide Others:
Acetylcholine Perchlorate
Benzyltrimethylammonium Dichloroiodate
Benzyltrimethylammonium Tetrachloroiodate
Benzyltrimethylammonium Tribromide
Betaine, Anhydrous
Betaine Hydrochloride
Bis(tetra-n-butylammonium)Dichromate
Bis(tetra-n-butylammonium)Tetracyanodiphenoquinodimethanide
L-Carnitine
3-[(3-Cholamidopropyl)dimethylammonio]-1-propanesulfonate
Denatonium Benzoate
n-Dodecyldimethyl(3-sulfopropyl)ammonium Hydroxide, Inner Salt
N-Fluoro-N'-(chloromethyl)triethylenediamine Bis(tetrafluoroborate)
n-Hexadecyltrimethylammonium Hexafluorophosphate
n-Hexadecyltrimethylammonium Perchlorate
n-Hexadecyltrimethylammonium Tetrafluoroborate
(Methoxycarbonylsulfamoyl)triethylammonium Hydroxide, Inner Salt
Neostigmine Methyl Sulfate
n-Octadecyldimethyl(3-sulfopropyl)ammonium Hydroxide, Inner Salt
Phenyltrimethylammonium Tribromide
Propionylcholine p-Toluenesulfonate
Tetra-n-butylammonium Azide
Tetra-n-butylammonium Bifluoride
Tetra-n-butylammonium Borohydride
Tetra-n-butylammonium Bromodiiodide
Tetra-n-butylammonium Dibromoaurate
Tetra-n-butylammonium Dibromochloride
Tetra-n-butylammonium Dibromoiodide
Tetra-n-butylammonium Dichloroaurate
Tetra-n-butylammonium Dichlorobromide
Tetra-n-butylammonium Difluorotriphenylsilicate
Tetra-n-butylammonium Difluorotriphenylstannate
Tetra-n-butylammonium Dihydrogentrifluoride
Tetra-n-butylammonium Diiodoaurate
Tetra-n-butylammonium Hexafluorophosphate
Tetra-n-butylammonium Hydrogensulfate [for Ion-Pair Chromatography]
Tetra-n-butylammonium Hydrogensulfate
Tetra-n-butylammonium Perchlorate
Tetra-n-butylammonium Perrhenate
Tetra-n-butylammonium Phosphate
Tetra-n-butylammonium Salicylate
Tetra-n-butylammonium Tetrafluoroborate
Tetra-n-butylammonium Tetraphenylborate
Tetra-n-butylammonium Thiocyanate
Tetra-n-butylammonium Tribromide
Tetra-n-butylammonium Triiodide
Tetraethylammonium Borohydride
Tetraethylammonium Perchlorate
Tetraethylammonium Tetrafluoroborate
Tetraethylammonium p-Toluenesulfonate
Tetraethylammonium Trifluoromethanesulfonate
Tetramethylammonium Acetate
Tetramethylammonium Borohydride
Tetramethylammonium Hexafluorophosphate
Tetramethylammonium Hydrogensulfate
Tetramethylammonium Perchlorate
Tetramethylammonium Sulfate
Tetramethylammonium Tetrafluoroborate
Tetramethylammonium p-Toluenesulfonate
Tetramethylammonium Triacetoxyborohydride
Tetra-n-propylammonium Perruthenate
Trifluoromethanesulfonic Acid Tetra-n-butylammonium Salt The polymers may include polymers of any of the foregoing monomers which are susceptible to polymerization. For example, in a preferred embodiment, the polymer comprises a polymer comprising at least two and up to one thousand monomeric units of diallyldimethylammonium chloride, (DADMAC), to form polyDADMAC, [2-(methacryloyloxy)ethyl]trimethylammonium chloride (TMMC), to form polyTMMC, quaternized vinyl pyridine (VP) derivatives, to give polyVP, or similar polymerizable quaternary amine monomers are utilized to form suitable quaternary amine polymers. The polymer, in one embodiment, is simply mixed with the gypsum core components. The polymer, in another embodiment, is simply sprayed onto the exterior of the front, back or both paper surfacing. The polymer, in another embodiment, is mixed with the gypsum core components, and is sprayed onto the exterior of the front, back or both paper surfacing. In another embodiment, the polymer is bonded directly to components of the gypsum core. For example, gypsum containing starch is susceptible to cerium initiated polymerization in which polymerization is initiated at carbons, hydroxyls or both of cellulosic substrates. In this embodiment, it is convenient to separately react the starch or cellulosic component with the antimicrobial monomer and initiator under conditions which benefit polymerization (heat, non-oxygenated atmosphere, high reaction concentration of monomeric antifungals and polymerization initiators). The starch or cellulosic component may be washed and recovered following polymerization, if desired, or may be added directly to the gypsum core in a concentration sufficient to achieve the desired function of the starch or cellulosic material. Variations on this methodology, of course, may be derived from this disclosure as the need arises, for example, to achieve desired characteristics for the gypsum core. Such variations derived from this disclosure are considered to come within the scope of equivalents to the methodology disclosed herein. In one embodiment, DADMAC monomers and an azo initiator are mixed with the cellulosic component, heated, washed and the antifungal and antimicrobial starch or cellulosic material is then mixed with the gypsum component of the core at different ratios to achieve the physico-chemical characteristics desired, while also imparting an antimicrobially active polymer to the gypsum core. In this manner, any moisture and fungal spores, bacteria or the like that may penetrate to the gypsum core are denied an environment conducive to their growth. This is very beneficial to address such issues as mold induced illnesses in buildings with circulating air handling systems (so-called "sick building syndrome"). Similar benefits are achieved by including polyDADMAC in the gypsum core. In this case, we have found that gypsum mixed with water alone and then dried rehydrates much more quickly than gypsum mixed with polyDADMAC and then dried.

In another embodiment, the polymer is covalently-bonded to fibers forming the paper surfacing of the gypsum, by cerium-catalyzed polymerization, or by the use of other free-radical initiators such as peroxides and azo compounds. Methods for polymerizing quaternary amine monomers are known in the art and are hereby incorporated by reference, for example, from PCT publication No. WO00033778; U.S. Pat. No. 4,076,663; see also George B. Butler, "Cyclopolymerization and Cyclocopolymerization", published by Marcel Dekker, Inc., New York, Basel, Hong Kong, ISBN: 0-8247-8625-4, 1992.

Without limiting the scope of the present invention, certain embodiments of the present invention may employ, in addition to the polymeric antifungal agent, cetyl pyridinium chloride (CPC) as an antifungal agent. The preferred embodiments are only exemplary. References herein to antifungal agents in general and CPC in particular are not intended to limit the scope of the invention.

Cetyl pyridinium chloride—also known as CPC or n-hexadecyl pyridinium chloride—is a cationic surfactant comprised of a hydrophilic quaternary ammonium moiety and a hydrophobic alkane moiety. CPC is commonly believed to possess biocidal activity due to its ability to bind readily to the negatively-charged cell walls of various microbes and to impact membrane integrity and function. It is a potent antifungal, antimycogen, and antibacterial chemical. CPC is commonly available in a powder form as a monohydrate manufactured by Zeeland/Cambrex and available from Johnson Matthey Catalog Company Inc. of Ward Hill, Mass., among others.

The preferred embodiments of the present invention employ an amount of PAA with or without CPC or other monomeric antifungal agents effective at inhibiting fungal, bacterial, and the like growth in or on the gypsum board. Preferably, the amount of PAA with or without CPC in and/or on the gypsum board is between about 0.01 and about 1.5 weight percent of the dry weight of the gypsum in the board. More preferably, the amount of PAA with or without CPC present in and/or on the gypsum board is between about 0.5 and about 1.0 weight percent of the dry weight of the gypsum in the board.

According to some preferred embodiments, the PAA with or without CPC is primarily present in the gypsum core. According to other preferred embodiments, the PAA with or without CPC is primarily located on one or both of the front and back paper facings, and more preferably on the outer surface of the front and back paper facings. According to yet other preferred embodiments, the PAA with or without CPC is primarily located in one or both of the front and back paper facings.

The present invention includes a novel method for the production of gypsum board comprising the addition of PAA with or without other antifungal agents during gypsum board manufacturing. The PAA antifungal agent is added during manufacturing in an amount that yields an effective amount of the antifungal agent in and/or on the board such that fungal, bacterial, and/or growth in and/or on the board is inhibited. Preferably, the finished gypsum board product comprises an amount of polymeric antifungal agent equal to from about 0.01 to about 1.5 weight percent of the dry weight of the gypsum in the board. More preferably, the finished gypsum board product comprises an amount of polymeric antifungal agent equal to from about 0.5 to about 1.0 weight percent of the dry weight of the gypsum in the board.

The gypsum board production process typically commences with the mining and transportation of gypsum rock. Once mined, the gypsum rock is crushed and ground into a fine powder. Alternatively, gypsum powder can be created synthetically. This powder is then subjected to a calcining process in which moisture is removed by heating. The novel gypsum board of the present invention may be prepared by any method capable of incorporating effective quantities of an agent having effective antifungal, antibacterial, and/or like activity into or onto the gypsum board product. Therefore, without limiting the scope of the present invention, the preferred embodiments of the present invention comprise mixing gypsum powder with water to form a gypsum slurry. Optionally, one or more of foam, pulp, starch and/or set-controlling agents may be added to the slurry.

The preferred embodiments of the present invention comprise a gypsum board manufacturing process in which the slurry is deposited between two unwinding rolls of absorbent paper on a conveyor belt. Conveyor belts useful in gypsum board processing typically reach lengths of from about 200 to about 1000 feet. This belt may be operated at a speed of from about 50 to about 200 feet per minute and typically at about 110 feet per minute. This process results in a continuous sandwich of gypsum core between the two paper layers or facings. Thus, the forming gypsum board is cast as a sheet having a three-layer structure: a gypsum core having front and back paper facings. The sandwich then passes through a forming station that establishes the width and thickness of the gypsum board. As the gypsum board moves along the belt line, the slurry reverts to a solid gypsum matrix. As the gypsum core molds and hardens, it becomes firmly bonded to the outer paper layers. Once formed, the continuous board is cut to a desired length and passed through dryers to remove excess moisture.

The preferred embodiments of the present invention also comprise the addition of the antifungal agent during the gypsum board manufacturing process. The antifungal agent may be added by any method capable of incorporating effective quantities of such agent into or onto the gypsum board product. Therefore, without limiting the scope of the present invention, the preferred embodiments of the present invention comprise adding the antifungal agent into and/or onto the gypsum core and/or by depositing the antifungal agent into and/or onto the front and/or back paper facings.

The polymeric antifungal agent with or without monomeric antifungal agents may be added to the gypsum slurry in any way capable of incorporating effective quantities of such agent into the gypsum core. Methods for adding PAA with or without CPC in solution form, powder form, or both during formation of the gypsum slurry include, but are not limited to, premixing PAA with or without CPC with the water, premixing the PAA with or without CPC with the gypsum powder, admixing the PAA with or without CPC with both the water and gypsum powder prior to or in the slurry mixer, or adding the PAA with or without CPC to a mixed gypsum slurry via a secondary or in-line mixer. In a preferred embodiment, dry PAA with or without CPC powder is added (via screw feeder) to dry gypsum powder prior to mixing with water to form the slurry. In another preferred embodiment, a PAA with or without CPC solution is co-metered with water to a slurry mixer and mixed with gypsum powder therein. The PAA with or without CPC solution preferably comprises from about 5 to about 20 weight percent PAA with or without CPC based on the total weight of the solution, provided however that the concentration and/or addition rate of the PAA with or without CPC solution can be adjusted to match the manufacturing conditions (such as line speed, in linear feet per minute) and product specifications (such as desired concentration of PAA with or without CPC in the final board product, board thickness, etc.). The amount of PAA with or without CPC and addition rate thereof is adjusted to achieve an effective amount of PAA with or without CPC in the gypsum board for inhibiting fungal, bacterial, and the like formation and growth thereon, as discussed previously.

In another preferred embodiment, the PAA with or without CPC solution is sprayed onto the front and/or back paper facings, which may occur at one or more points in the manufacturing process. For example, the PAA with or without CPC solution can be sprayed onto the paper facings prior to or as they are unrolled to form the sheets, after the sheets have been formed, before and/or after drying the sheets, and/or after the sheets have been cut into boards. Furthermore, the PAA with or without CPC may be sprayed onto the inner surface, the outer surface, or both of the front and/or back paper facings. Preferably, the PAA with or without CPC solution for spraying comprises from about 5 to about 20 weight percent PAA with or without CPC based on the total weight of the solution. In another embodiment, the PAA with or without CPC may be added to one or both of the paper facings during manufacture of the paper facings. Adding PAA with or without CPC to the front and/or back paper facing (by either spraying or during manufacture of the paper) may be in addition to or as a substitute for adding PAA with or without CPC to the gypsum core of the board as described above. Thus, gypsum boards may have the following configurations: PAA with or without CPC treated core and untreated facings; untreated core and one or both PAA with or without CPC treated facings; PAA with or without CPC treated core and one or both PAA with or without CPC treated facings; PAA covalently linked to components of the core, with or without CPC admixed, with neither paper surface, one paper surface or both, either coated with PAA with or without CPC, or one or both paper surfaces covalently bonded with PAA with or without a coating of CPC.

Antifungal agents such as CPC frequently exhibit some toxicity to humans and animals. Consequently, minimizing human and animal exposure to CPC and other antifungal agents is desirable. Furthermore, the gypsum board should maintain its antifungal efficacy over an extended period of time. The present invention provides a polymeric antifungal agent (the PAA) which significantly enhances the longevity and efficacy of the antifungal agent, with or without monomeric antifungals being present, such as the CPC. In addition, the gypsum board products may be specifically formulated to release an active antifungal agent slowly over time or upon becoming wet such that the antifungal properties and activity of the board are maintained at an effective level over time, in addition to the extended efficacy of the PAA. The preferred embodiments also include methods for making same. For example, a time-release antifungal agent may comprise an active antifungal agent combined with additional materials such as polymer binders or encapsulators to achieve the desired release profile of the active antifungal ingredient from the board over time or upon wetting.

In a preferred embodiment, in addition to the presence of PAA, active antifungal agent such as CPC is included with an encapsulator such as J5MS Methocel hydroxypropyl methylcellulose, available from the Dow Chemical Company. Alternatively, an active ingredient such as CPC may be physically adhered within the gypsum core (for example, encapsulated by calcium within the gypsum core) or on/in the paper facings such that the CPC is released upon wetting of the gypsum core and/or paper facings. Methods for encapsulating active materials to achieve controlled release over time and/or upon wetting are well-known and any such methods and processes are within the scope of the present invention. For certain applications, the presence of the PAA is sufficient, however, and the incorporation of CPC or the like with or without binders is not necessary.

To initiate polymerization of quaternary amine monomers, cerium ion is useful to target covalent linkage of the growing polymer chains to cellulosic substrates. In addition, Azo compounds such as AIBN (2,2'-azobisisobutyronitrile) are commonly used as initiators for vinyl polymerizations, but are not generally thought of as catalysts for preparation of graft copolymers. We have found, however, that a water-soluble derivative of AIBN (2,2'-Azobis[N-(2-carboxyethyl)-2-methylpropionamidine]tetrahydrate, or VA-057, available from Wako Specialty Chemicals) was a suitable initiator for the graft polymerization of quaternary vinyl monomers onto cellulosic substrates such as paper or onto starch substrates. AIBN, which is one of the most commonly used polymerization initiators, is not soluble in water; and thus cannot be used directly in aqueous solutions. AIBN is soluble in alcohols, however, and thus can possibly be used as an initiator for the graft polymerization of quaternary monomers onto cellulose since the monomers are also soluble in alcohols. It is also likely that AIBN could be used in an emulsion system in order to achieve similar results. Other potentially useful Azo initiators include: (2,2'-Azobis[2-(5-methyl-2-imidazolin-2-yl)propane]dihydrochloride, or VA-041; 2,2'-Azobis{2-methyl-N-[1,1-bis(hydroxymethyl)-2-hydroxyethyl]propionamide, or VA-080; 2,2'-Azobis(2 -methylpropionamide)dihydrochloride, or V-50; 2,2'-Azobis(N-cyclohexyl-2-methylpropionamide), or Vam-111; 1,1'-Azobis(cyclohexane-1-carbonitrile); all available from Wako Specialty Chemicals, Inc.; and numerous other similar compounds).

Organic peroxides such as benzoyl peroxide (BPO) are also widely used as polymerization initiators. Just as in the case of AIBN (above), BPO is not water soluble, but it can possibly be used in alcoholic solution in order to graft quaternary vinyl monomers onto cellulose. Other potentially useful peroxide initiators include: (dicumyl peroxide, t-butyl peroxide, methylethylketone peroxide, and a variety of other peroxides, peroxyketals, peroxydicarbonates, and hydroperoxides). These and numerous other potentially useful catalysts are available from a variety of suppliers such as Lucidol-Penwalt, and Akzo.

Combinations of two or more of the initiators described above are also effective. These catalysts or initiators can also be used to form crosslinked cellulose-quaternary grafted materials.

In a preferred embodiment, the gypsum board is formed by a process in which paper surfaces, either prior to or after application to the gypsum core, are sprayed with a combination of reactive monomer and polymerization initiator. The polymerization mixture is typically aqueous, and is preferably flash heated once in contact with the desired paper surface, (front, back or both, either with or without application of non-polymerizable antifungals, or previously polymerized antifungals, either before or after the flash heating step) to initiate polymerization. In this manner, the polymerization reaction can be initiated in a controlled fashion at the desired point in the gypsum board assembly process. If necessary, a glue, preferably a glue containing a fungicide, such as that disclosed in US Patent Publication 2003/0027889, is used to assist in adhering the paper to the gypsum core. No washing step is required, as any unpolymerized monomeric antifungal agent, such as DADMAC or TMMC, will have some potentially beneficial effect as a leachable antifungal. Should it be desirable, however, to remove these unreacted components, a brief rinse step following flash polymerization may be included. In this event, it may be preferable to treat the paper facing material prior to adhesion to the gypsum core.

In connection with the paper component associated with wallboard, those skilled in the art will appreciate based on this disclosure that there are many methods of treating the paper to achieve the desired antimicrobial properties taught herein. According to one method, pulp is treated and used to make paper, optionally including blending with untreated pulp. Paper prepared in this manner was found to pass the ASTM method for mold growth.

In another embodiment, the outer surface of the wallboard paper is treated before it is used in making the wallboard. Although the paper is treated on one side only, the paper can be used on both sides of the wallboard. The treated side is preferably oriented outward, away from the gypsum core. The antimicrobial polymer coating is non-uniform throughout the paper, and concentrated at the surface, thus the surface is more fungal resistant than the inside of the paper. A useful range of between 1 and 5 wt %, relative to the weight of the paper, may be utilized.

In a further embodiment, a crosslinker is included to extend the degree of polymerization of the PAA. If the polymerization reaction is run under air, and without the crosslinker, the degree of polymerization can be low. During the course of polymerization, grafting of polymer occurs. Where a three-dimensional crosslinker is utilized, there is some network (gel) formation. This can result in the formation of a partial interpenetrating network (OPN), which further locks the polymer to the paper. The IPN can be formed between individual paper fibers, or within the pores of an individual fiber, or both. Without wishing to be limited to mechanism, although some of the IPN is possibly not covalently bonded, it is nevertheless "permanently" attached to the paper. It is anticipated that some soluble homopolymer is formed as well. Although the soluble homopolymer is not bound to the paper, it is only expected to represent a relatively small fraction of the total polymer present. Accordingly, it will be appreciated from this disclosure that what is intended by PAA includes all combinations of grafted, IPN, and soluble polymer. A preferred polymer crosslinker is to be N,N'-methylenebisacrylamide, since it is highly water-soluble, and miscible with high DADMAC monomer concentrations. Other crosslinkers can be ethoxylated trimetholoylpropane triacrylate (SR9035, Sartomer Co.), polyethylene oxide diacrylate (SR344, Sartomer co.), or other di, tri, or polyfunctional monomers. Water-soluble crosslinkers are preferred, and crosslinkers completely soluble and miscible with the monomer solution are most preferred. Solvents such as alcohols can be used to compatibilize the monomer/crosslinker solutions if needed.

In further embodiments according to this invention, formulations are utilized wherein soluble linear DADAMC homopolymer is added to the coating solution. This increases the viscosity of the solution, and provides a so-called "leveling effect", i.e. it produces smoother coatings. Naturally, the added polymer is not bonded to the paper, but it nonetheless serves an antimicrobial utility. The combination of mobile and bonded antimicrobial polymer is preferred in certain applications in that it combines fast action with prolonged efficacy.

We have discovered that the appearance of the treated paper can be improved by first wetting the paper surface with water. This allowed a higher amount of polymer to be applied uniformly, without mottling or discoloration of the paper. Prewetting was applied at a rate of approximately 1 to 3 grams water per square foot of paper.

Curing of the paper (polymerization) may be carried out in a variety of formats. For example, in some applications according to this invention, curing was successfully carried out by radiant heating under a heat lamp, at a distance of approximately three inches for between 10 and 60 seconds, or by application of heat from heating metal plates, rollers, presses, or the like, set at appropriate temperatures, for between 10 and 30 seconds. A particularly useful method was to place two wet sheets of paper face-to-face, prior to heating with a heated metal surface. This prevented contact of the wet surface with the hot metal surface. Radiant heat, hot-presses or rollers, microwaves, and steam are all optional methods for curing of the polymer.

Monomer solutions may be applied according to this invention by dipping, spraying, or roller application. The use of squeegees, doctor blades or air curtains are useful for controlling the coverage rate.

Antimicrobial testing used in certain examples disclosed herein involves bacterial testing, or fungal testing. Bacterial challenge test is considerably more rapid and less costly than the ASTM mold growth test. It, nonetheless, serves as a convenient screening tool to determine general antimicrobial efficacy. We have found that a high kill rate for bacteria in the tests performed as disclosed herein generally correlates with efficacy in the mold/fungus challenge.

In a preferred embodiment according to this invention, the PAA is utilized as a complexing agent for monomeric ionic antifungal compounds. In one aspect of this embodiment of the invention, the PAA is utilized to "stabilize" an otherwise easily removed or diffusible antimicrobial, such as sodium pyrithione (SP). In the discussion which follows, SP is referred to specifically, both as a specific compound utilizable according to this invention, but also as an example of a class of ionic (whether anionic or cationic) antifungal compounds that may be bound by the polymeric antifungal agent (PAA), which itself may be polycationic, as where the polymer is a polyquaternary amine, or polyanionic. We have found that pyrithione is significantly bound by polyquaternary amine PAA, and resists leaching much better than from untreated substrate.

Two recent US patent applications discuss the use of sodium pyrithione in wallboard applications (US #2004/0005484 and US #2003.0234068, both of which are hereby incorporated by reference for this purpose). Both contain good general overviews of SP and related antifungal materials. It is noted that SP is very water soluble (i.e. >50 wt % aqueous solutions are possible). This makes it relatively easy to wash or leach the SP from the treated surface. Zinc pyrithione (ZP) may be used in place of or in addition to SP in wallboard applications. The solubility of zinc pyrithione is much less than SP (max. solubility in waster is 0.0015%). The average useful level of pyrithione in the gypsum slurry (as indicated in the 0005484 application) is about 250 ppm (=0.025%). It is unclear as to what level this represents at the surface of the paper; however, the discussion in that application indicates that the level in the paper facing would be similar. Since this level far exceeds the solubility of zinc pyrithione, it would be difficult to achieve using the zinc salt. Apparently, this is the gist of the discussion in paragraph 17 of that application. Paragraph 19 describes the stabilization of SP by the calcium in the gypsum core. The wallboard according to the present invention achieves this function more efficiently than calcium, which itself is monomeric and potentially leacheable. Using a sufficiently high level of bonded polyquaternary amine as the PAA according to this invention, yields a dual mode of protection, assuming that only a small fraction of the quaternary amine sites are bonded to pyrithione (e.g. if 4% polyquat is utilized with 250 ppm SP, there is a vast excess of free polyquaternary amine sites). Even if all of the SP eventually migrates out of the panel (by contact with excessive moisture, for instance) the bonded polyquat continues to provide antimicrobial effect. In addition, utilizing SP in combination with polyquaternary amine also allows much lower polyquat levels to be used, since the SP level is low, and only a comparable amount of polyquat is needed for stabilization. In this case, the antimicrobial contribution from the polyquat is reduced due to shielding by the bound SP. However, there is a cost savings from using less polyquat, and as SP is removed, the revealed polyquat sites continue to provide long-term antimicrobial efficacy.

Accordingly, polyquat bonded to the paper stabilizes the sodium pyrithione and decreases the amount that can be washed off by a given amount of water. The SP is added to the wet gypsum slurry, and allowed to migrate into the paper, where it is stabilized, or it is applied directly to the quat-treated paper. Alternatively, or in addition, SP is mixed with DAMAC monomer prior to paper treatment. The quat-treated paper is also, optionally, or in addition, treated with SP separately, either before or after quat is applied to the paper. In yet a further option according to this invention, quat-treated starch is used to stabilize the SP in the gypsum core. Even if the quat is not bonded to the paper, it nonetheless stabilizes the SP to some extent. Since DADAMC homopolymer has a high molecular weight, it diffuses much more slowly than SP, thereby retarding diffusion away from the wallboard component of the SP bound to the homopolymer. In addition, the solubility of the quat:SP complex is expected to be less than that of either component alone.

Having generally described the invention and methods of making and using this invention, certain specific examples are provided below which disclose specific methods for making antifungal gypsum board comprising polymeric antifungal agents. While these examples are provided to disclose the best mode and preferred embodiments, these examples should not be construed as limiting on the scope of the present invention, which instead should be understood through reference to the appended claims.

EXAMPLES

Example 1

First and second sets of 0.5 inch thick sample gypsum boards comprising about 0.5 and about 1.0 weight percent CPC, respectively, based on the dry weight of the gypsum in the board are produced. The board manufacturing line is run at a speed of 255 linear feet per minute, and separate 5-minute trials are conducted for each set of sample boards. For each five minute trial, the total water in the gypsum slurry is 1133 pounds per thousand square feet per minute of run time (lbs/MSF/min), for a total of 5665 lbs and the total dry gypsum powder is 1300 lbs/MSF/min of run time, for a total of 6500 lbs. For the 0.5% PAA with or without CPC board, 0.005.times.6500=32.5 lbs of PAA with or without CPC is added to the slurry as a 15 weight percent PAA with or without CPC solution, based on total weight of the solution. For the 1.0% PAA with or without CPC board, 0.01.times.6500=65.0 lbs of PAA with or without CPC is added to the slurry as a 15 weight percent PAA with or without CPC solution, based on total weight of the solution. A total of about 5000 square feet of each set of boards is produced.

Testing is expected to indicate that PAA with or without CPC-treated gypsum board effectively suppresses bacterial and fungal growth. It is currently believed that appropriately treated gypsum board will exhibit broad-based resistance to a wide variety of microbes.

Example 2

In this example, polyDADMAC is formed by polymerization of DADMAC monomers in the presence of a polymerization initiator in an inert atmosphere, in the presence of a gypsum board component, selected from: the front or back paper facings, the pulp used to make the front and back paper facings, the starch included as a component of the gypsum core, or another component to which the nascent polymer becomes covalently bonded as it is formed. Appropriate polymerization initiators are known, including various salts of cerium. Alternatively, an initiator such as a so-called "Azo" initiator, such as VA-057, V-50 and the like, available from Wako Pure Chemical Industries, is utilized. Other initiators, including but not limited to hydrogen peroxide, sodium persulfate ("SPS"), and the like are utilized to advantage according to this invention to initiate polymerization Example 3

In this example, polyDADMAC is formed by polymerization prior to contact of the polymer with a gypsum board component. An appropriate amount of polyDADMAC is then mixed with the gypsum core components or is sprayed onto the paper facing components of the gypsum board, either prior to or after the paper is affixed to the gypsum core.

Example 4

In this example, polyDADMAC is formed by polymerization prior to contact of the polymer with a gypsum board component. An appropriate amount of polyDADMAC is then mixed with the gypsum core components and is sprayed onto the paper facing components of the gypsum board, either prior to or after the paper is affixed to the gypsum core.

Example 5

In this example, polyDADMAC is formed by polymerization prior to contact of the polymer with a gypsum board component. An appropriate amount of polyDADMAC is then mixed with the gypsum core components and is sprayed onto the paper facing components of the gypsum board, either prior to or after the paper is affixed to the gypsum core. In this example, a non-polymeric antifungal agent, such as cetyl pyridinium chloride, is also included in the gypsum core, the paper facings, or both, either with or without binders or retention aids.

Example 6

In this EXAMPLE, starch or cellulosic components of gypsum board, whether from the core or the paper facings, is reacted with antimicrobial monomer and initiator under conditions which benefit polymerization (heat, non-oxygenated atmosphere, high reaction concentration of monomeric antifungals and polymerization initiators). The starch or cellulosic component is washed and recovered following polymerization. Alternatively, that component is added directly to the gypsum core or paper facing material in a concentration sufficient to achieve the desired function of the starch or cellulosic material. For this example, DADMAC monomer is reacted at a final concentration (v/v) of about 25-50%, while TMMC monomer is reacted at a final concentration of about 5-25%. An initiator is mixed with the starch or cellulosic component containing reactive monomer, heated, washed and the antifungal and antimicrobial starch or cellulosic material is then mixed with the gypsum component of the core or paper facing at different ratios to achieve the physicochemical characteristics desired, while also imparting an antimicrobially active polymer to the gypsum core, paper facing or both In this manner, any moisture and fungal spores, bacteria or the like that may penetrate to the gypsum core are denied an environment conducive to their growth. This is very beneficial to address such issues as mold induced illnesses in buildings with circulating air handling systems (so-called "sick building syndrome").

Example 7

In this EXAMPLE, 5 g of gypsum stucco was mixed with 2.5 g water (Sample A). In Sample B, 5 g of gypsum stucco was mixed with 2.5 g 1% aqueous polyDADMAC. The thus formed gypsum stucco material was allowed to dry into 2 cm×1 cm×0.5 cm chunks. Exposure of Samples A and B by immersion in water revealed that Sample A was water saturated within 2 minutes, while sample B was only about half-saturated after 20 minutes (by visual inspection of cross-sectioned chunks of Samples A and B. Accordingly, we conclude that gypsum core treated in this manner with polyDADMAC has unexpected property of increased water resistance.

Example 8

In this example, polyDADMAC is formed by polymerization prior to contact of the polymer with a gypsum board component. An appropriate amount of polyDADMAC is then mixed with the gypsum core components and is sprayed onto the paper facing components of the gypsum board, either prior to or after the paper is affixed to the gypsum core.

Example 9

In this example, a non-polymeric antifungal agent, such as cetyl pyridinium chloride, is also included in the gypsum core, the paper facings, or both, either with or without binders or retention aids.

Example 10

In this example, gypsum board is formed by a process in which paper surfaces, either prior to or after application to the gypsum core, are sprayed with a combination of reactive monomer and polymerization initiator. The polymerization mixture is, and is flash heated once in contact with the desired paper surface, (front, back or both, either with or without application of non-polymerizable antifungals, or previously polymerized antifungals, either before or after the flash heating step) to initiate polymerization. The final concentration of polyDADMAC formed on the thus treated surfaces is about 0.5 to 1.5% of the total mass of paper. Of this, approximately 10% to 99% of the DADMAC is converted to polyDADMAC which is covalently linked to the paper and does not leach. The polymerization reaction is initiated in a controlled fashion at the desired point in the gypsum board assembly process. In one variation, a glue containing a fungicide disclosed in US Patent Publication 2003/0027889, is used to assist in adhering the paper to the gypsum core. No washing step is required as any unpolymerized monomeric antifungal agent, such as DADMAC or TMMC, remains as a leachable antifungal. Nonetheless, in a variation, unreacted components are removed by a brief rinse step following flash polymerization.

Example 11

A solution containing 50 mL of DADAMC monomer (65 wt % solution, Aldrich Chemical Co.), 0.75 grams of sodium persulfate (Acros Chemical) dissolved in 10 mL water, 10 grams of 40% polyDADMAC solution in water (AF6545, Axchem, Inc), and 30 mL distilled water was prepared. Sheets of wallboard facing paper measuring 6"×6" were cut. Each sample weighed approximately 5.4 grams. The paper sheets were wiped with a damp sponge to moisten the surface. The amount of water applied was between 0.0 and 0.6 grams per sheet. Immediately after moistening, the monomer solution was applied using a foam rubber paint roller. Excess monomer solution was applied, and then leveled using a silicone rubber squeegee and light hand pressure. The samples were then weighed again to determine the amount of monomer solution applied, which was between 0.1 and 0.5 grams per sheet. The samples were then immediately cured by placing them on an aluminum pan three inches under a red 250 watt incandescent reflector bulb (Heat Ray—Westinghouse). Samples were moved under the bulb for between 10 and 60 seconds to ensure even heating and to prevent hot spots or charring. The coated samples were tested for uniformity and durability of coverage by soaking 1"×1" cut squares in 0.5% bromthymol blue (BTB) solution for 10 seconds, followed by rinsing under running tap water for ten seconds. Samples were then placed into 1 liter of water containing a small amount of ammonia, and evaluated periodically over the course of several hours. Samples prepared as described in this paragraph exhibited a distinct and uniform blue coloration, which persisted for at least six hours or more, even with continuous stirring. Untreated paper was colorless after the initial rinsing. Samples treated in the same manner, except without the use of crosslinker exhibited a distinct blue color; however, this color faded more quickly after soaking in ammonia solution. Samples prepared without using the prewetting step showed less uniformity of color.

Samples of wallboard paper treated in the above manner were tested according to a modified AATCC 100 method: Samples were cut into ¾"-1" squares and autoclaved for 20 min., then subsequently immersed into saline solution (PBS) until saturated. After saturation wallboard samples were inoculated with 100 microliters of $10^{-2}$ dilution (~$3 \times 10^6$ CFU) of overnight culture (S.Aureus). Inoculated samples were then incubated for 18 hours at 37 C and 95% RH. After incubation samples were placed in 50 ml tubes containing 15 ml saline solution (PBS) and shaken vigorously. After removing samples from tubes sample elutes were diluted and plated for population count. The content of the polymeric antimicrobial coating was determined from the weight of coating solution applied. Samples containing 0%, 1.2%, 2.0%, and 4.0% polymer were tested. The results are presented below, and indicate that the coated paper has good antimicrobial efficacy:

| Sample | S. Aureus (CFU) |
|---|---|
| Wallboard paper W-7 (2.0%) | $3 \times 10^1$ |
| | $1 \times 10^1$ |
| | $1 \times 10^1$ |
| Wallboard paper W-10 (1.4%) | $1 \times 10^1$ |
| | $<2 \times 10^0$ |
| | $<2 \times 10^0$ |
| Wallboard paper W-11 (4.0%) | $<2 \times 10^0$ |
| | $<2 \times 10^0$ |
| | $<2 \times 10^0$ |
| Wallboard paper (untreated, as received) | $1.4 \times 10^4$ |
| | $1.2 \times 10^4$ |
| Control | $1.4 \times 10^4$ |

Example 12

This example demonstrates the production of antimicrobial wallboard paper using wood pulp grafted with a quaternary ammonium polymer. Brown wood pulp produced from recycled corrugated cardboard was used in this experiment. The wood pulp was mixed with a solution of DADMAC monomer, SPS initiator, and water, and then heated to effect graft polymerization. The treated wood pulp was thoroughly rinsed to remove any soluble polymer. The graft level was approximately 10 wt % based on the observed weight gain. The treated wood pulp was subjected to the BTB dye test described above, and was found to give a persistent, uniform, dark blue color. Hand sheets of paper, approximately 12" square were made using a lab-scale screen type papermaking process. Paper was made using 100% treated wood pulp, as well as 75/25, 50/50, and 25/75 blends with untreated pulp. The finished paper had good mechanical and physical properties, and was similar to paper made form 100% untreated pulp. The BTB dye test applied to the papers showed a blue color intensity proportional to the amount of treated pulp in the composition. The treated paper was subjected to antimicrobial testing as described above, and was found to have good antimicrobial properties. In addition, samples of paper made from 100% wood pulp were sent to a commercial testing laboratory for evaluation of mold and mildew resistance according to ASTM method #D3273. The results demonstrate a high antifungal activity for the paper prepared from wood pulp grafted with quaternary ammonium polymer.

Example 13

This example demonstrates the stabilization of pyrithione by a cationic cellulose surface. A nonwoven rayon gauze material (SofWick, a commercially available rayon gauze material manufactured by Johnson & Johnson) was graft polymerized with diallyldimethylammonium chloride (DADAMC) to 10 weight % poly(DADMAC), to form the cationic cellulose surface. Each gauze substrate treated in this manner measured approximately 40 square inches. One gram samples of cationic cellulose prepared in this manner (sample K), and untreated SofWick (sample L) were each soaked overnight in 25 ml of 0.5% SP solution. Samples were removed and squeezed to remove excess liquid. Samples were then washed in 25 mL of distilled water for one hour with agitation, and then squeezed to remove excess liquid. Each sample was subjected to four sequential extractions using 25 mL of distilled water for one hour at room temperature with agitation. Samples were squeezed to remove excess solution between extraction cycles. A fifth extraction was performed using pH 7.4 phosphate buffered saline (PBS). Saline is expected to remove a greater amount of pyrithione due to ion exchange. The extract solutions were tested for antimicrobial activity by placing single 20 microliter drops of the solutions at marked locations on an agar culture plate spread with ~$3 \times 10^3$ CFU (continuous lawn) of S. aureus bacteria. Plates were incubated overnight at 37° C., and the diameter of the "zone of inhibition", or "ZOI" was measured. The size of this zone corresponds to the antibacterial activity (and therefore the antifungal activity) of the extract solutions. Results are listed below:

| Extraction # | Cationic Cellulose ZOI diameter (mm) | SofWick: ZOI diameter (mm) |
|---|---|---|
| 1 | 12 | 0 |
| 2 | 11 | 0 |
| 3 | 14 | 0 |
| 4 | 12 | 0 |
| 5 (saline) | 27 | 0 |

SP control solutions exhibited the following ZOI (0.1% SP: 26 mm; 0.01% SP: 12 mm). This example clearly shows the binding and stabilization of SP by the cationic cellulose substrate. Sodium pyrithione was completely removed from untreated rayon after a single washing; however, a significant amount of SP remained on the cationic cellulose sample, even after washing four times in a 25× excess of water. The large increase in activity after the final extraction in saline shows that a considerable amount of SP remained bonded to the cationic cellulose after the first four extractions in distilled water, and also confirms the lack of any initial SP binding to the untreated cellulose. It is expected that SP bound to cationic wallboard paper (cellulose) as substrate behaves in the same manner as shown in this example.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention.

Accordingly, the scope of protection is not limited by the description set out above, but is only limited by the claims which follow, that scope including all equivalents of the subject matter of the claims. Each and every claim is incorporated into the specification as an embodiment of the present invention. Thus the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications and publications cited herein are hereby incorporated herein by reference, to the extent that they provide exemplary, procedural or other details supplementary to those set forth herein.

What is claimed is:

1. An antifungal gypsum board comprising a gypsum core, front paper facing, and back paper facings, wherein a polymeric antifungal agent is covalently bonded, by use of an initiator, to at least one of said paper facings, and wherein said polymeric antifungal agent is selected from the group consisting of polyDADMAC, polyTMMC, and quaternized polyvinyl pyridine derivatives.

2. An improved method for manufacturing a gypsum board comprising covalently bonding, by use of an initiator, a polymeric antifungal agent to the board or a component thereof, adding a non-polymeric antifungal agent to the board or a component thereof, wherein the polymeric antifungal agent is polycationic or polyanionic, and wherein, the non-polymeric antifungal agent is stabilized by the polymeric antifungal agent, whereby the non-polymeric antifungal agent resists leaching.

3. The method of claim 2 further comprising encapsulating or binding the non-polymeric antifungal agent such that the non-polymeric antifungal agent is released over time, upon exposure to moisture, or both.

4. The method of claim 2 wherein, in addition to the polymeric antifungal agent, a non-polymeric_antifungal agent is included in the gypsum board or a component thereof, selected from the group consisting of chlorhexidine, alexidine, cetyl pyridinium chloride, benzalkonium chloride, benzethonium chloride, cetalkonium chloride, cetrimide, cetrimonium bromide, glycidyl trimethylammonium chloride, stearalkonium chloride, hexetidine, sodium pyrithione, zinc pyrithione, triclosan and triclocarban.

5. The method of claim 4 wherein the non-polymeric antifungal agent comprises cetyl pyridinium chloride, pyrithione, or both.

6. The method of claim 5 wherein the polymeric antifungal agent is added in an amount equal to between about 0.01 weight percent and about 1.5 weight percent of the dry gypsum in the gypsum board.

7. An improved process for manufacturing gypsum board comprising covalently bonding, by use of an initiator, an antifungal agent to a paper to be used as a front or back paper facing in the gypsum board, wherein said improvement comprises said antifungal agent being a polymeric antifungal agent selected from the group consisting of polyDADMAC, polyTMMC, and quaternized polyvinyl pyridine derivatives.

8. The process of claim 7 wherein, in addition to a polymeric antifungal agent, an additional non-polymeric antifungal agent is included in the gypsum board or a component thereof selected from the group consisting of chlorhexidine, alexidine, cetyl pyridinium chloride, benzalkonium chloride, benzethonium chloride, cetalkonium chloride, cetrimide, cetrimonium bromide, glycidyl trimethylammonium chloride, stearalkonium chloride, hexetidine, sodium pyrithione, zinc pyrithione, triclosan and triclocarban.

9. A method for making an antifungal gypsum board which comprises treating starch or cellulosic components of gypsum board, whether from the core or the paper facings, with antimicrobial monomer and initiator under conditions which benefit polymerization, optionally washing and recovering the starch or cellulosic component following polymerization, and combining the thus treated starch or cellulosic component with other desired components and at relative concentrations to produce said antifungal gypsum board in which DADMAC monomer is reacted at a final concentration (v/v) of about 25-50%, or TMMC monomer is reacted at a final concentration of about 5-25%; an initiator is mixed with the starch or cellulosic component containing reactive monomer DADMAC or TMMC monomers the thus treated component is heated, washed and the antifungal and antimicrobial starch or cellulosic material is then mixed with the gypsum component of the core or paper facing at different ratios to achieve the physico-chemical characteristics desired, while also imparting an antimicrobially active polymer to the gypsum core, paper facing or both.

10. An improved gypsum board comprising a polymeric antifungal agent formed by a process comprising applying to paper surfaces, either prior to or after application to a gypsum core, a combination of reactive monomer and polymerization initiator, flash heating the reactive monomer and polymerization initiator once in contact with the desired paper surface to initiate polymerization, wherein said polvmeric antifungal agent is selected from the group consisting of polyDADMAC, polyTMMC, and quaternized polyvinyl pyridine derivatives.

11. An antifungal gypsum board comprising a polymeric antifungal agent which is polycationic or polyanionic and a non-polymeric antifungal agent which is stabilized by the polymeric antifungal agent, wherein said polymeric antifungal agent is covalently bound by use of an initiator to a component of the gysum board, and whereby the non-polymeric antifungal agent resists leaching.

12. The antifungal gypsum board of claim 11, wherein the polymeric antifungal agent is polycationic and the non-polymeric antifungal agent is a pyrithione compound.

13. The antifungal gypsum board of claim 11, wherein the polymeric antifungal agent is a poly(quaternary amine).

14. The antifungal gypsum board of claim 13, wherein the polymeric antifungal agent is polyDADMAC.

15. The antifungal gypsum board of claim 1, wherein the polymeric antifungal agent is polyDADMAC.

* * * * *